United States Patent [19]

Bell

[11] 4,381,681
[45] May 3, 1983

[54] PARTICULATE SAMPLE COLLECTOR

[75] Inventor: John P. Bell, Raleigh, N.C.

[73] Assignee: The United States of America as represented by the Administrator of the Environmental Protection Agency, Washington, D.C.

[21] Appl. No.: 213,799

[22] Filed: Dec. 8, 1980

[51] Int. Cl.³ .............................................. G01N 1/24
[52] U.S. Cl. .................................................. 73/863.03
[58] Field of Search ........... 73/863.02, 863.03, 863.23, 73/28; 55/210

[56] References Cited

U.S. PATENT DOCUMENTS

| 1,517,144 | 11/1924 | Anderson | 73/28 |
| 3,438,179 | 4/1969 | Jouault . | |
| 3,841,145 | 10/1974 | Boubel . | |
| 3,859,842 | 12/1974 | Crosby . | |
| 4,123,932 | 11/1978 | Baker . | |
| 4,159,635 | 7/1979 | Sehmel . | |
| 4,246,788 | 1/1981 | Olin | 73/863.03 |

OTHER PUBLICATIONS

Kurz, J. L., et al., *A New Flow Controller for High Volume Air Samplers*, for Presentation AI Annual Meeting Air Pollution Control Asso., Jun. 1975.

Stevens, R. K., et al., *Sampling of Atmospheric Sulfates and Related Species* Atmosphere Environment, vol. 12, pp. 55-68, Pergamon Press, 1978, Great Britain.

Harrison, W. K., Jr., et al., *Constant Flow Regulators for High-Volume Air Sampler*, Industrial Hygiene Journal, vol. 21, Apr. 1960, pp. 115-120.

Patterson, R. K., *Aerosol Contamination from High-Volume Sampler Exhaust*, APCA Journal, vol. 30, No. 2, Feb., 1980, pp. 169-171.

*Primary Examiner*—S. Clement Swisher

[57] ABSTRACT

A particulate sample collector has a blower to draw air through ducting in which a filter collects particles. The blower is driven by a sealed inductive A.C. motor. A throttle in the ducting is controlled by a pneumatic motor in response to variation in pressure drop, to provide constant mass flow rate as the filter gradually becomes clogged.

13 Claims, 3 Drawing Figures

U.S. Patent      May 3, 1983      4,381,681
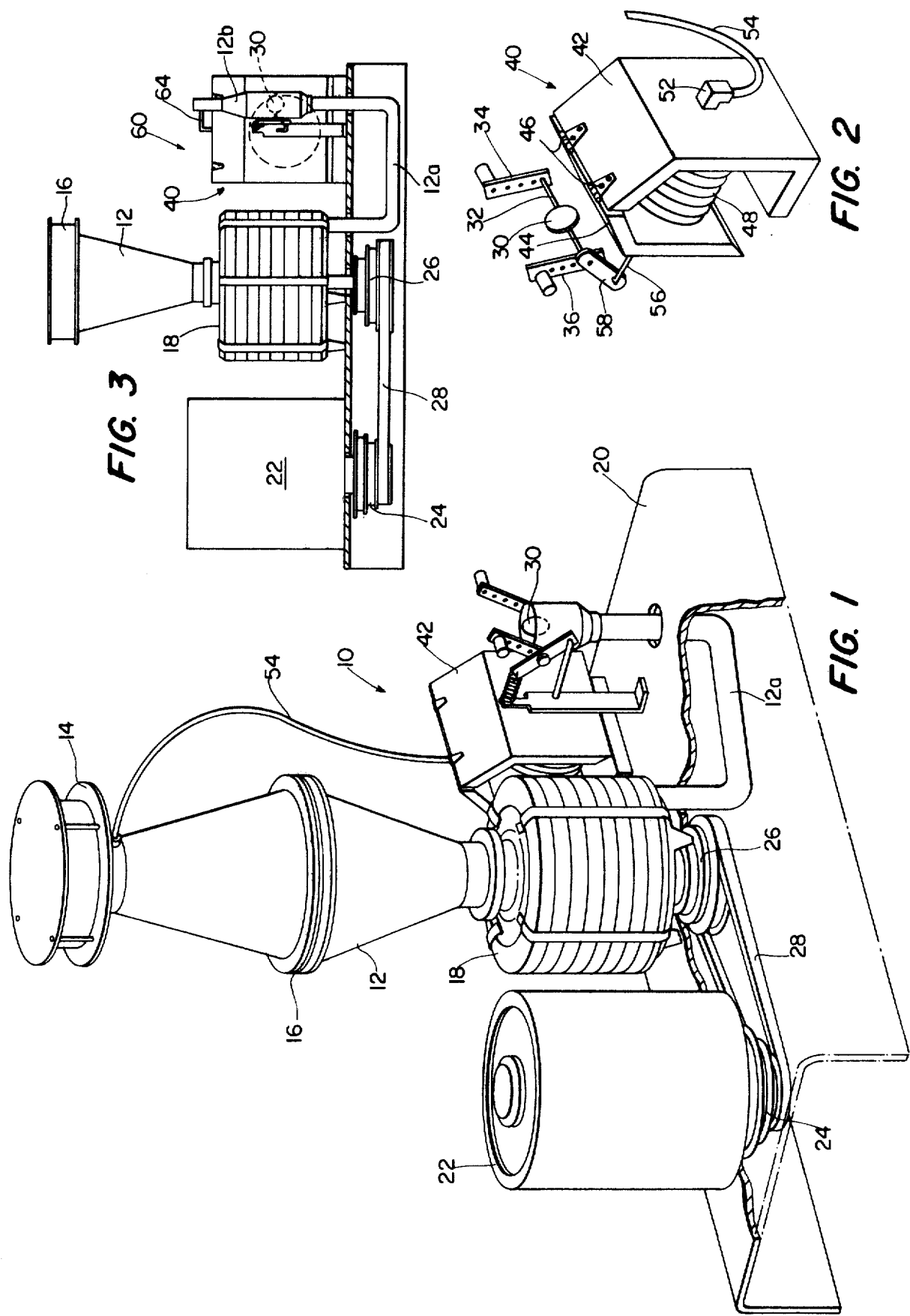

PARTICULATE SAMPLE COLLECTOR

BACKGROUND OF THE INVENTION

The present invention relates to sample collectors for sampling the particulate material in the atmosphere.

The determination of the degree of pollution in the atmosphere has received increasing attention in recent years. To make this determination, it is desirable to determine the number and kinds of particles in the atmosphere at various locations, and equipment has been provided for this purpose. Such equipment, known as particulate sample collectors, generally includes a filter, an apparatus for moving air through the filter, such apparatus normally including a duct in which the filter is placed, and a motor and blower, the motor actuating the blower to thereby cause the air to move through the duct. It is recognized that the particles which are collected by the filter tend to clog the filter, thereby gradually reducing the amount of air being drawn through the filter.

The particulate sample collectors are required to be placed in locations where they are subjected to various rigorous weather conditions. Being exposed to the atmosphere, they are subjected to rain storms, wind storms and temperatures from substantially below freezing to above 120° F.

The problem of the gradual clogging of the filter has drawn the proposed solution of providing electronic circuitry to alter the flow rate through the filter as it becomes clogged; this presents the difficulty that the electronic circuitry is not reliable in all weather conditions, and is initially very expensive.

Particulate sample collectors heretofor known have provided a duct system in which the electric motor for driving the blower was placed. This electric motor was of the direct current type, having brushes, and it has been found that as the motor is operated, the brushes wear, emitting carbon into the atmosphere and some of this emitted carbon from the brushes of the DC motor had found to be recycled onto the filter, thus causing erroneous readings. For example, in a rural area, where 30 mg. has been collected on a filter, tests have indicated that as much as 28 mg. can be contamination from the brushes of the motor, and tests have indicated that whether the motor is up stream or down stream of the filter, the range of contamination from the motor has been from 2 to 28 mg., where the filter collected 30 mg. of such particles.

Yet another problem which has been found to have occurred in particulate sample collectors is that the rate of flow through the filter and duct has varied due to variations in the electric energy supplied to the electric motor, from conventional power lines. This has been a source of error in measuring the amount of air pollution or contamination.

Among the prior art known to applicant is the article "A New Flow Controller For High Volume Air Samplers" by Jerome L. Kurz and John. G. Olin of Sierra Instruments, Inc., Carmel Valley, Calif., presented at the 68th Annual Meeting of the Air Pollution Control Association, Boston, Mass., June 15-20, 1975; this paper describes a high volume sampler utilizing a hot wire filament with an electric feed back system to actuate a valve; this has such defects as noted above or being unreliable in some weather conditions and also being unduly expensive. In the article entitled "Sampling and Analysis of Atmospheric Sulfates and Related Species" by Robert K. Stevens and Thomas G. Dzubay, Atmospheric Environment, Volume 12, pg. 55, there is disclosed an apparatus for obtaining a constant flow rate in a sampler by utilizing a pressure regulator in the pump exhaust, the pressure regulator sensing the differential between atmospheric pressure and pressure in the exhaust line. The article "Constant Flow Regulators for the High-Volume Air Sampler" by Walter K. Harrison, Jr., John S. Nader and Frank S. Fugman, Journal of Industrial Hygiene, Vol. 50, page 574, discloses in FIG. 4 a constant flow regulator which is a variable restrictor placed in series in the flow line from the filter, a spring being utilized to counter-act pressure on a piston, to vary the outlet area as the flow rate would tend to decrease when the filter is clogged, and thereby maintain the flow rate constant.

Also of interest is "Aerosol Contamination from High-Volume Sampler Exhaust" by Ronald K. Patterson, APCA Journal, Vol. 30, No. 2, which illustrates a sampler which includes a motor within the duct system.

Baker et al U.S. Pat. No. 4,123,932 discloses an apparatus for monitoring a working area in which air is pumped through a so called "dosimeter"; as the filter becomes clogged, the flow rate is sensed by differential pressures across the discharge orifice from the pump, and a feed back loop, which includes electronic circuits, is used to control the speed of the motor which drives the pump. This apparatus, accordingly, requires a sophicated electronic circuit, which is expensive, and is the kind of apparatus which has not proven to be reliable in all weather conditions.

Jouault U.S. Pat. No. 3,438,179 provides a sampling apparatus including a blower for drawing air through a filter; down stream of the filter is a disc, to which oil is supplied. As the filter becomes clogged, less oil is fed to the disc, so that there is provided a constant flow rate over the entire sampling period. This apparatus requires a highly sophisticated arrangement, including a supply of oil and the partial clogging of a filter with the oil, and is therefore unsatisfactory for all air sampling uses.

Sehmel U.S. Pat. No. 4,159,635 discloses a filter in which a blower is down stream of the filter element. In this construction, a wind speed sensor controls an inlet opening to the filter and to the motor of the blower.

Boubel U.S. Pat. No. 3,841,145 discloses an apparatus for measuring particulate emissions in gas flows, and is used for sampling air over a very short period of time, such as one minute. This device is used, for example, for sampling gas in an exhaust stack and utilizes a manually operated exhaust valve.

Bosch U.S. Pat. No. 3,859,842 is another illustration of a gas sampler for an exhaust stack, and discloses the utilization of a diaphragm motor for controlling a butterfly valve in a by-pass conduit.

SUMMARY OF THE INVENTION

The present invention provides a high volume particulate sample collector having a duct with a filter therein, a blower in the duct for causing air to move through it, and a motor, specifically a brushless alternating current induction motor, which is sealed, positioned externally of the duct, and drivingly connected to the blower, as by a belt-and-pulley arrangement. A high volume of flow is achieved through the particulate sampler collector, of up to 2,500 liters per minute. There is provided in the duct, preferably at the outlet or discharge portion thereof, a back pressure control valve, a butterfly valve being preferred. This butterfly control valve is moved so as to maintain constant flow rate through the duct, the flow rate being sensed by a pneumatic conduit connected to a pneumatic motor. The pneumatic motor has a bellows and a movable portion, and suitable linkage connects the movable portion of the pneumatic motor with the valve, so as to cause the valve to move to a more open position, as the flow through the filter and duct decreases, the flow rate being sensed by the pneumatic conduit. Thus, flow rate is maintained relatively constant over a long period of time, at a relatively high volume of flow, regardless of changes in temperature, line condition of the electric current fed to the electric motor, and of the clogging of the filter with the collected sample. In alternate embodiments, the pneumatic conduit may have the end thereof opposite the pneumatic motor either at the inlet or at the outlet of the duct.

Among the objects of the present invention are to provide a high volume particulate sample collector which will have a constant flow rate therethrough irrespective of the gradual clogging of the filter, variations and temperature and/or variations in line current to the motor. It is another object to provide such a collector which is economical to construct, and reliable in use in adverse weather conditions, and which does not, itself, serve to provide erroneous readings by contaminating the environment of the collector. Other objects and many of the attendant advantages of the present invention will be more readily understood from the following specification, claims and drawings.

BRIEF DESCRIPTION OF THE DRAWING

FIG. 1 is a perspective view, with parts removed, of a particulate sample collector in accordance with the present invention.

FIG. 2 is a view taken on the line 2—2 of FIG. 1.

FIG. 3 is an elevational view of an alternate embodiment of a particulate sample collector.

DESCRIPTION OF THE PREFERRED EMBODIMENTS

Referring now to the drawings, wherein like or corresponding reference numerals are used to designate like or corresponding parts throughout the several views, there is shown in FIG. 1 a particulate sample collector 10 which includes a duct 12 having at its inlet end a fractionator 14. Fractionator 14 is a known device for separating particles into different size ranges. The particulate sample collector 10 is a high volume collector, and includes a filter 16, of known construction. The duct 12 has therein a blower 18, which is preferably an 8-stage centrifugal blower. Blower 18 is mounted on a supporting base 20. Laterally of blower 18 and outside of duct 12 there is a motor 22. Motor 22 is a brushless motor, preferably an induction AC electric motor. The output shaft of the motor 22 has a step-pulley 24 thereon, and the blower is provided with a step-pulley 26, a belt 28 engaging the pulleys. The step-pulleys 24 and 26 provide for speed changes.

The outlet of the blower 18 has connected to it a final duct portion 12a of the duct 12, which has an outlet portion 12b.

A valve 30 of the butterfly type is mounted on a shaft 32 extending through the outlet portion 12b, and a pair of arms 34 and 36 are provided on the shaft 32. The arm 34 carries a weight 34a, which may be positioned in any one of a number of holes in the arm 34, so as to thereby adjust the moment arm acting on the shaft 32. The arm 36 is of the same construction as the arm 34, carrying a weight 36.

Referring now to FIG. 2, the pneumatic motor 40 is shown mounted on the base 20, and includes a first, fixed portion 42, a second, movable portion 44, the portions being connected together by hinges 46. Extending between the portions 42 and 44 is a bellows 48, the ends of which are hermetically sealed to the inner sides of the portions 42 and 44. A fitting 52 extends through the portion 42, and air conduit 54 is connected to the fitting 52, thereby communicating with the interior of the bellows 48. A rod 56 is connected to the movable portion 44 of pneumatic motor 40, and to a lever 58, to which one end of the shaft 32 is connected. There may also be seen in FIG. 2 the arms 34 and 36, as well as the butterfly valve 30.

Referring again to FIG. 1, the conduit 54 may be seen to be connected to the duct 12, adjacent the inlet thereof, in order to sense the flow through the duct 12.

In operation, air is caused to flow through the duct 12 by the blower 18, driven by motor 22. The air is discharged through the outlet portion 12b of the duct 12, and the throttle valve 30 will have the position thereof changed by the pneumatic motor 40, which operates in response to variation in the mass flow rate through the duct 12. More particularly, as the filter 16 becomes clogged, as particles contained in the air are deposited in the filter or are trapped by it, there will be a decrease in the rate of the mass flow of air, and this decrease will be sensed by the conduit 54 and relayed to the pneumatic motor 40, which will operate the valve 30 in order to gradually compensate for the gradual clogging of the filter 16.

In FIG. 3 there is shown an alternate embodiment 60, including a duct 12 having a filter 16 at the enlarged inlet end, and including a portion immediately down stream of filter 16 which tapers inwardly, to the entrance of blower 18. Blower 18 is actuated by the motor 22 through the pulleys 24 and 26 and the belt 28; it will be understood that the blower 18, motor 22 and pulleys and belt in the particulate sample collector 60 are substantially the same as those in the particulate sample collector 10. Further, the outlet 12b of the duct 12 includes a valve 30, which is actuated from a pneumatic motor 40, the constructions of which are the same as those which are shown in FIG. 2.

In contrast to the construction of FIGS. 1 and 2, however, the particulate sample collector 60 has a conduit 64 which has the inlet or sensing end thereof connected in communication with the duct 12 at the outlet portion 12b thereof, the air conduit 64 otherwise being similar to the air conduit 54, and connected to the pneumatic motor 40, and particularly to the interior of the bellows 48 so as to thereby cause movement of the pneumatic motor 40 in response to pressure drop within the duct 12. Accordingly, the embodiment of FIG. 3, like the embodiment of FIGS. 1 and 2, utilizes the pneumatic motor 40 to actuate the butterfly type throttle valve 30, applying a back pressure on the blower 18. With this arrangement, the pressure drop across a constant flow resistance in the duct system remains constant, and therefore the mass flow remains constant.

With the apparatus as disclosed in FIGS. 1-3 hereof, not only will the mass flow remain constant over an extended period of time as the filter becomes gradually more clogged, but in addition the mass flow will remain constant irrespective of variation in line current supplied to the motor.

It will be appreciated that the apparatus as herein disclosed, in both of its embodiments, avoids the defects of the prior art, including the emission of carbon into the atmosphere from the brushes of the previously used direct current motor.

It will be obvious to those skilled in the art that various changes may be made without departing from the spirit of the invention, and therefore the invention is not limited to what is shown in the drawings and described in the specification but only as indicated in the appended claims.

I claim:

1. A high volume particulate sample collector comprising:
   (a) duct means for conducting air,
   (b) means for causing air to flow through said duct means,
   (c) a filter in said duct means,
   (d) means for maintaining constant mass flow rate through said duct means comprising valve means having substantially the same operating characteristics as a rotary butterfly valve, said valve means having an actuator movable between limiting positions and a valve element movable between open and shut positions corresponding to said actuator limiting positions, pneumatic motor means for moving said valve means comprising a movable element movable over a substantial distance, means for connecting said movable element to said actuator for movement of said actuator by said movable element, and pneumatic conduit means responsive to pressure drop in said duct means for operating said motor.

2. A particulate sample collector in accordance with claim 1, wherein said filter is in said duct means upstream of said flow causing means.

3. A particulate sample collector in accordance with claim 1, wherein said valve means is located in said duct means down stream of said flow causing means.

4. A particulate sample collector in accordance with claim 1, said pneumatic motor means comprising a bellows.

5. A particulate sample collector in accordance with claim 4, and further comprising adjustable weight means for counterbalancing movement of said valve.

6. A particulate sample collector in accordance with claim 1, said pneumatic conduit means comprising a conduit extending from adjacent the inlet of said duct means to said pneumatic motor means.

7. A particulate sample collector in accordance with claim 1, and further comprising fractionating means at the inlet of said duct means.

8. A particulate sample collector in accordance with claim 1, said air flow causing means comprising a blower, an electric motor, means mounting said electric motor laterally of said blower and duct means and exteriorly thereof, and means for drivingly connecting said motor to said blower.

9. A particulate sample collector in accordance with claim 8, wherein said motor is a sealed alternating current induction motor.

10. A particulate sample collector in accordance with claim 8, wherein said motor is a brushless electric motor.

11. A particulate sample collector in accordance with claim 1, wherein said pneumatic conduit means comprises a conduit extending from adjacent the discharge end of said duct means to said pneumatic means.

12. A high volume particulate sample collector comprising:
    (a) duct means for conducting air,
    (b) a filter in said duct means,
    (c) means for causing air to flow through said duct means comprising a blower, a brushless electric motor laterally of said blower and exteriorly of said duct means, means for drivingly connecting said electric motor and said blower, and means for maintaining the flow rate through said duct means constant as the filter becomes clogged said means for maintaining constant mass flow rate through said duct means comprising valve means in said duct means having substantially the same operating characteristics as a rotary butterfly valve, including a valve element movable between fully open and fully closed positions upon movement of an actuator movable between limits corresponding to said open and closed positions, pneumatic motor means for moving said actuator comprising a movable element movable over a substantial distance, means for connecting said movable element to said actuator for movement of said actuator by said movable element of said motor means, and pneumatic conduit means responsive to pressure drop in said duct means for operating said pneumatic motor means.

13. The particulate sample collector of claim 12, wherein said electric motor is an AC induction motor.

* * * * *